United States Patent [19]

Smith et al.

[11] Patent Number: 5,597,530

[45] Date of Patent: Jan. 28, 1997

[54] PROCESS FOR PREFILLING AND TERMINALLY STERILIZING SYRINGES

[75] Inventors: Gary N. Smith, Libertyville; John C. Tanner, II, Lake Buff, both of Ill.

[73] Assignee: Abbott Laboratories, Abbott Park, Ill.

[21] Appl. No.: 638,397

[22] Filed: Apr. 26, 1996

Related U.S. Application Data

[63] Continuation of Ser. No. 532,027, Sep. 21, 1995, abandoned, which is a continuation of Ser. No. 292,676, Aug. 18, 1994, abandoned.

[51] Int. Cl.$^6$ .............................. A61L 2/00; A61L 9/00; B65B 1/20
[52] U.S. Cl. .......................... 422/28; 422/100; 422/102; 422/302; 141/11; 141/91; 141/326; 134/94.1; 134/150; 134/166 R
[58] Field of Search .............................. 422/28, 100, 102, 422/302; 141/11, 91, 326; 134/94, 150, 166 R

[56] References Cited

U.S. PATENT DOCUMENTS

| | | | |
|---|---|---|---|
| 3,561,596 | 2/1971 | Knox | 206/63.2 |
| 3,935,883 | 2/1976 | Stach et al. | 141/27 |
| 4,628,969 | 12/1986 | Jurgens, Jr. et al. | 141/1 |
| 4,718,463 | 1/1988 | Jurgens, Jr. et al. | 141/11 |
| 5,093,079 | 3/1992 | Bakaitis | 422/28 |
| 5,207,983 | 5/1993 | Liebert et al. | 422/25 |
| 5,338,303 | 8/1994 | King et al. | 604/110 |
| 5,364,369 | 11/1994 | Reynolds | 604/187 |

*Primary Examiner*—Nina Bhat
*Attorney, Agent, or Firm*—Brian R. Woodworth

[57] ABSTRACT

A method of prefilling and terminally sterilizing a syringe including providing a syringe barrel having first and second opposite ends where the first end includes a port therethrough with a connector member formed about an exterior of the port and the second end being open. Particulate matter is removed from the interior of the syringe barrel and a cap and stopper are sterilized, the stopper including first and second opposite longitudinal ends. The first end of the stopper is inserted into the second open end of the syringe barrel until the first end of the stopper reaches the first end of the syringe barrel. The syringe barrel then is filled with a desired liquid, such as a medicament or imaging agent, through the port of the first end of the syringe barrel so that substantially no air enters the syringe barrel and where the stopper moves within the syringe barrel from the first to the second ends thereof upon filling. The cap then is connected to the connector member of the first end of the syringe barrel to seal the port and then the syringe barrel, stopper, luer cap and liquid within the syringe barrel are terminally sterilized in a autoclave having a spray over-pressure cycle which maintains pressure about the exterior of the syringe barrel at least equal to the pressure within the interior of the syringe barrel.

10 Claims, 3 Drawing Sheets ns, is a continuation of appli-
5,597,530

PROCESS FOR PREFILLING AND TERMINALLY STERILIZING SYRINGES

This application is a continuation of application Ser. No. 08/532,027, filed Sep. 21, 1995, is a continuation of application Ser. No. 08/292,676, filed Aug. 18, 1994 both abandoned.

TECHNICAL FIELD

The present invention relates generally to prefilled syringes, and more particularly to a process or method for terminally sterilizing a glass or plastic syringe filled with medicament, an imaging agent or any other liquid for parenteral administration that utilizes a cost effective straight line process.

BACKGROUND OF THE INVENTION

Medical instruments and devices typically are provided to a practitioner in a sterile condition. This particularly is true of such instruments that are utilized for providing a desired medicament, imaging agent or other liquid for parenteral administration, such as a hypodermic syringe or the like.

A syringe typically includes some type of barrel, vial or cartridge having a desired medicament, imaging agent or other liquid therein for parenteral administration and is manufactured sterile primarily by two methods. The first method utilizes aseptic techniques and includes, for example, individually sterilizing the elements of the syringe, assembling the elements, filling the syringe with a desired medicament in an aseptic environment and packaging the assembled syringe for later use. This method, however, is susceptible to contamination during the assembly and packaging of the device.

A second method is referred to as "terminal sterilization" where the completely assembled syringe filled with medicament is sterilized, typically by steam, and then packaged for later use. Such a method or process ensures that the medicament, imaging agent or other contents of the syringe, as well as the individual syringe elements, are provided in a sterile condition at the point of use.

Terminally sterilizing a prefilled device containing a desired medicament, such as a syringe, typically is accomplished with steam in an autoclave. The heat and pressure generated in the autoclave, however, can have an adverse effect on the device.

For example, vapor pressure and thermal expansion of the medicament in the syringe can cause the syringe sealing members, such as a stopper or end cap, to blow out. Additionally, if the barrel or other elements of the syringe are formed from plastic, the heat and pressure generated by the autoclave can deform these members and inhibit their performance during use.

An example of an existing method for terminally sterilizing prefilled syringes is illustrated in U.S. Pat. No. 4,718,463. That patent substantially discloses washing the barrel of the syringe with repeated water jet washings, preferably ten washings, filling the barrel through its open end, assembling the piston in the open end, sealing the syringe and its contents and then autoclaving the assembled and sealed syringe. During autoclaving, the pressure on the outside surfaces of the syringe is maintained at least equal to the pressure of the syringe contents and the syringe is preferably heated to a temperature between 120° and 125° C.

With this method, however, filling the syringe and inserting the plunger or piston through the open end of the syringe barrel requires complex filling and sealing equipment. Additionally, when filling and sealing from the open end of the syringe barrel, a selected amount of inert gas is included within the barrel which is not acceptable in many applications. Also, sterilizing between 120° and 125° C. limits syringe barrel material choices, particularly material which would have improved clarity.

Another example of an existing method for terminally sterilizing prefilled syringes is illustrated in U.S. Pat. No. 5,207,983. That patent substantially discloses steam sterilizing of a syringe by autoclaving where 2–10% empty space is provided between the plunger and the distal or closed end of the syringe barrel and at least 10% empty space is provided between the plunger and the proximal or open end of the syringe barrel. The 10% empty space allows for sliding movement of the plunger toward the proximal end of the barrel in response to internal pressure generated during autoclaving and preferably requires at least one temperature/ pressure measuring device in direct contact with the contents of at least one sample syringe for monitoring and regulating temperature and pressure within the autoclave.

With this method, however, no initial cleaning or steam sterilization prior to terminal sterilization is required, but a more complicated autoclaving process is utilized. Initial cleaning removes any particulates which may be present within the syringe barrel or other elements which may cause contamination while steam sterilization insures microbial "kill" and maintains a necessary degree of moisture within the syringe elements, particularly the stopper or plunger.

Furthermore, this method would appear to provide less medicament with the same size syringe due to the requirement of at least 10% empty space within the syringe to allow for plunger expansion. Although a larger syringe can be utilized to provide the same measured amount of medicament which is customary in the medical field, a larger syringe could be confusing to a practitioner and may require different packaging. Additionally, if the proper plunger expansion room is not provided or the preferred conditions within the autoclave are not maintained, the plunger will blow out of the syringe.

It therefore would be desirable to provide a process or method for prefilling and terminally sterilizing syringes which substantially eliminates air within the syringe barrel, does not require expansion space for the stopper and terminally sterilizes the filled syringe without deforming the syringe or causing the stopper or plunger to blow out. Such a process not only ensures a sterilized filled syringe but eliminates air from the syringe barrel that could cause plunger blow out or be ejected out of the syringe by a practitioner.

SUMMARY OF THE INVENTION

The present invention provides a method or process of prefilling and terminally sterilizing a syringe. The process includes providing a syringe barrel having first and second opposite ends where the first end includes a port therethrough with a luer lock connector formed about an exterior of the port and the second end being open.

Particulate matter is then removed from the interior of the syringe barrel and a luer cap and stopper are sterilized, the stopper including first and second opposite longitudinal ends. The first end of the stopper is inserted within the second open end of the syringe barrel until the first end of the stopper reaches a position against the first end of the syringe barrel.

The syringe barrel then is filled with a desired liquid, such as a medicament or imaging agent, through the port of the first end of the syringe barrel so that substantially no air enters the syringe barrel. At the same time, the stopper moves from the first end to the second end of the syringe barrel upon filling.

A luer cap is inserted over the luer lock connector member of the first end of the syringe barrel and the prefilled and assembled syringe barrel, stopper and luer cap are terminally sterilized in an autoclave having a spray over-pressure or steam-air mixture cycle which maintains pressure about the exterior of the syringe barrel at least equal to or greater than the pressure within the interior of the syringe barrel.

The syringe barrel can be formed from glass, plastic or any other material and the autoclave preferably has a maximum temperature of between 116° and 120° C. Removal of particulate matter from the syringe barrel preferably is accomplished with a de-ionized air wash while the sterilization of the luer cap and stopper preferably is provided by washing, siliconizing and steam sterilizing the luer cap and stopper.

After terminally sterilizing the prefilled syringe, drying can be provided with compressed, oil-free air or by means of a drying cycle in the autoclave, and a plunger can be secured to the second end of the stopper. Additionally, a label having a lot number and date can be applied to the prefilled syringe and the syringe can be packed into a carton which in turn is packed into a case. Upon filling the case with a desired number of cartons, the case is sealed and checked for accuracy by high-speed weighing.

Numerous other advantages and features of the present invention will become readily apparent from the following description of the invention, the claims and the accompanying drawings.

DESCRIPTION OF THE PREFERRED EMBODIMENTS

While this invention is susceptible of embodiment in many different forms, the specification and the accompanying drawings specifically disclose one or more forms as examples of the invention. The invention is not intended to be limited to the embodiments described, the scope of the invention being pointed out in the appended claims.

For ease of description, the method and assembly of this invention is described in the normal, upright, operating position and terms such as upper, lower, horizontal etc. are utilized with reference to this position. It will be understood, however, that the apparatus of this invention may be manufactured, stored, transported and sold in an orientation other than the position described.

Some of the figures illustrating the embodiment of the assembly or process of the present invention show conventional components, structural details and mechanical elements that will be recognized by one skilled in the art. The detailed descriptions of such elements, however, are not necessary to an understanding of the invention and, accordingly, are not presented herein.

Figure 1:
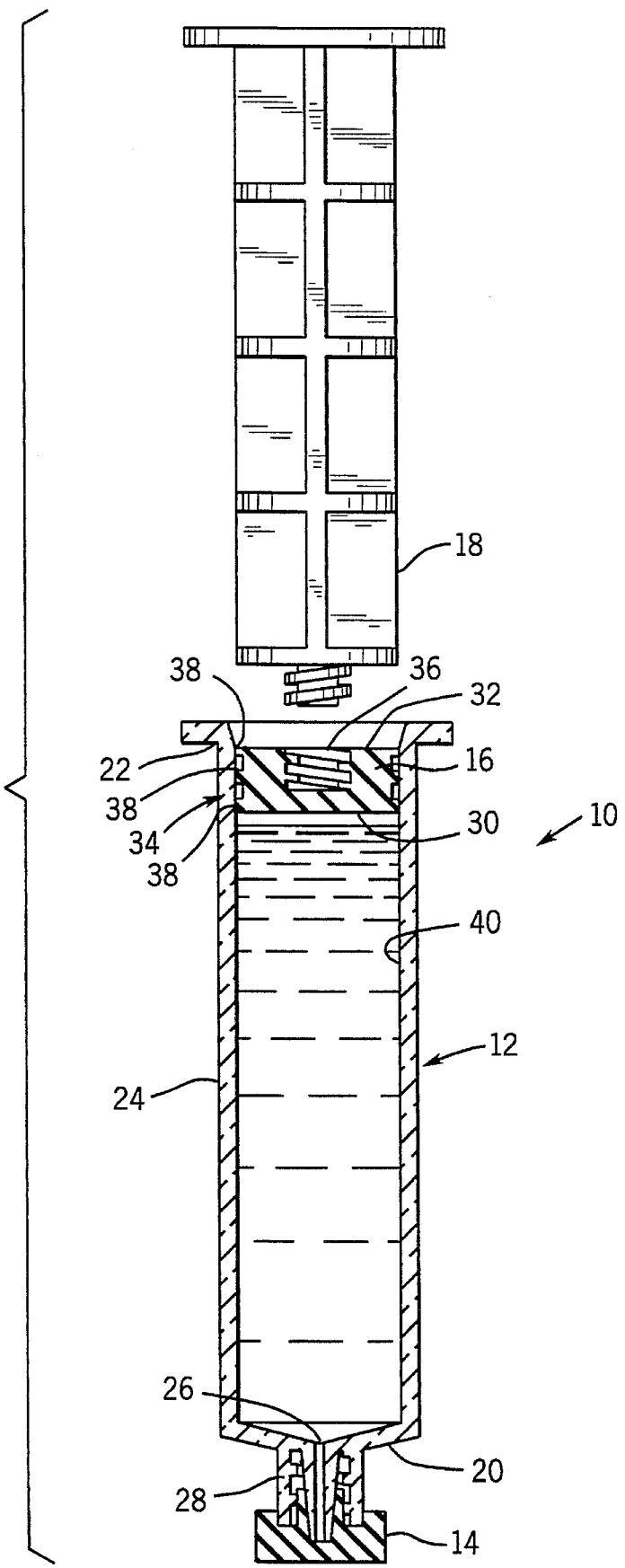
FIG. 1 is a longitudinal cross-sectional view of a prefilled syringe assembly which is terminally sterilized by the process of the present invention with a plunger member shown separately therefrom.

Referring to FIG. 1, a prefilled syringe assembly produced by the process or method of the present invention is generally designated by the reference numeral 10. The syringe 10 includes a syringe barrel 12, a cap 14, a stopper 16 and a plunger 18.

The barrel 12 includes first and second opposite ends 20 and 22 and a cylindrical wall 24 therebetween. The barrel 12 preferably is formed from glass or plastic such as polypropylene or polyethylene and, if desired, can be radiation resistant. Alternatively, the barrel 12 can be formed from any type of plastic or other material if desired.

To enable a medicament, imaging agent or other liquid to exit the first end 20 upon advancement of the stopper 16 within the barrel 12 during use, the first end 20 includes a port 26 therethrough defining an elongate channel. To connect a needle assembly or similar member (not illustrated) to an exterior of the first end 20, a connecter member 28, such as a luer lock connector or the like, is formed on the exterior of the first end 20 about the port 26. After filling of the syringe 10 as described below, the cap 14, which preferably is formed from rubber as a pull or peel-off cover member, is attached about the luer lock connector member 28 to seal the port 26 of the first end 20 of the syringe 10.

The stopper 16 preferably is formed from a resilient material, such as rubber or the like, and includes a first interior end 30, a second opposite exterior end 32 and a cylindrical side wall 34 extending therebetween. The second end 32 preferably includes a threaded recess 36 for threaded engagement with the plunger 18. Alternatively, the plunger 18 can be press-fit to the second end 32 of the stopper 16 or can be attached in any other desired way.

Depending on the size of the syringe 10, the stopper 16 can be provided with the plunger 18 pre-assembled thereto. Alternatively, the stopper 16 and plunger 18 can be provided separately, particularly with larger size syringes 10, and must be assembled during the present process.

The cylindrical side wall 34 of the stopper 16 preferably includes a plurality of engagement ribs 38 for sealing engagement with an interior surface 40 of the barrel 12. Although three ribs 38 are illustrated, the number of ribs 38 can vary.

It is to be noted that in order to obtain a good seal between the stopper 16 and the barrel 12 and enable sealed, sliding engagement therebetween for proper dispersion of the medicament or other liquid out of the port 26, the stopper 16 and the barrel 12 must be provided with a certain amount of siliconization before assembly. During terminal sterilization as described below, the interior end 30 of the stopper 16 is provided moisture from the medicament while the exterior end 32 is provided moisture from the steam of the autoclave.

Moisture for the ribs 38 and the spaces between the ribs 38, however, must be provided in the material of the stopper 16 itself before the stopper 16 is inserted within the barrel 12 and preferably maintained until the syringe 10 is used. The present invention provides such moisture by steam sterilizing the stopper 16 prior to insertion within the barrel 12 to drive moisture into the rubber of the stopper 16. Thereafter, the stopper 16 is inserted within the barrel 12 with minimal delay to prevent drying of the stopper 16 before insertion within the barrel 12. Accordingly, during terminal sterilization, the moisture within the material of the stopper 16 is drawn out to provide moisture to the ribs 38 and areas therebetween.

Figure 2:
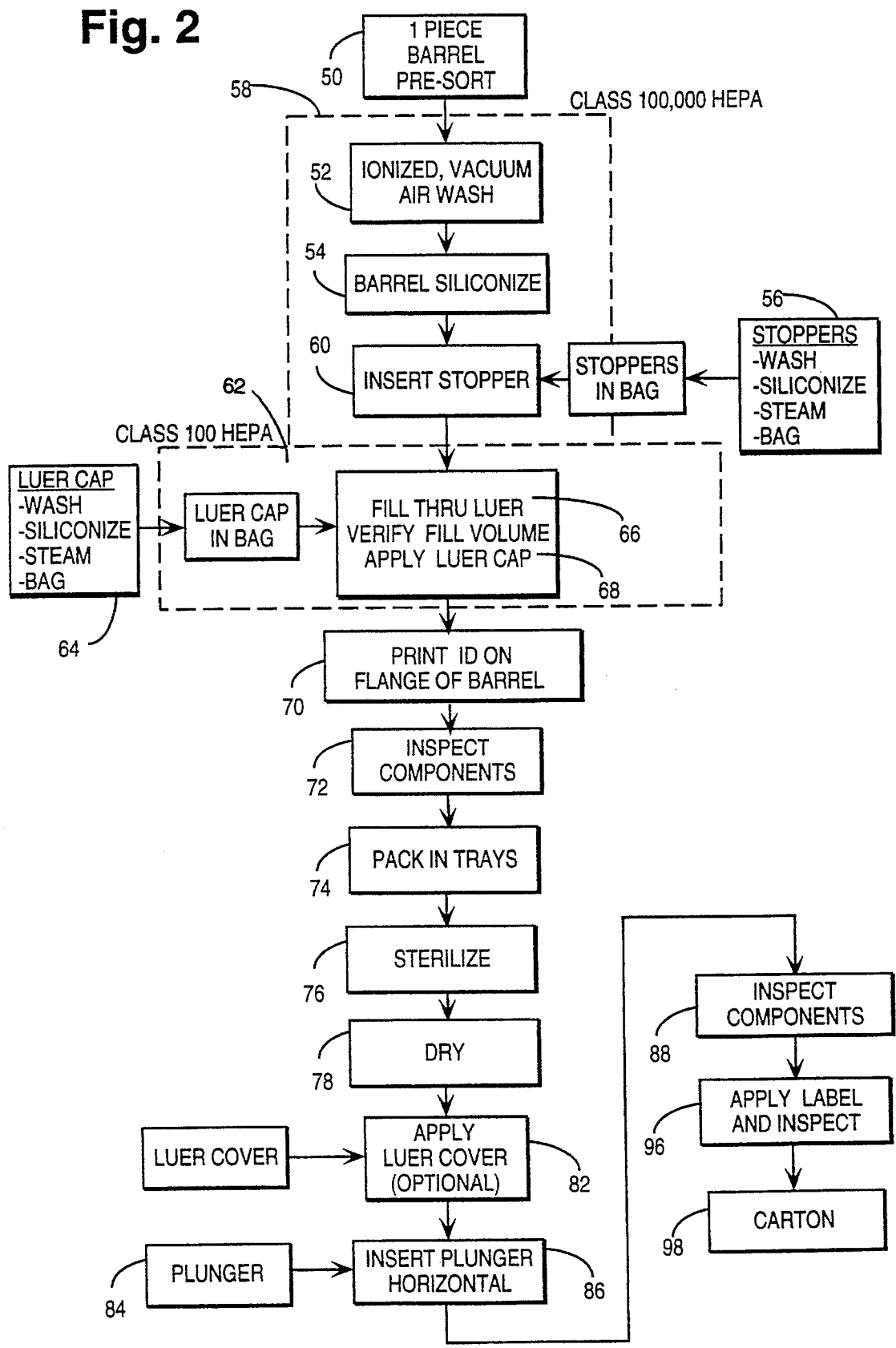
FIG. 2 is a flow chart illustrating an embodiment of the terminal sterilization process of the present invention.

Referring to FIG. 2, an embodiment of assembling, prefilling and terminally sterilizing syringes 10 according to the present invention now will be described.

As noted briefly above, the entire process of the present invention preferably is performed in a "straight line" process with minimal delay between steps. This ensures a good manufacturing process or GMP where the particular elements are processed on a first in, first out basis with virtually no storage of elements between steps. Accordingly, initial preparation of the barrel 12, luer cap 14 and stopper 16 prior to assembly is conducted substantially simultaneously.

With regard to initial processing of barrels 12, the barrels 12 typically are formed or molded using clean techniques to reduce the amount of particulate matter as much as possible and are provided in plastic bags, double bagged in plastic bags or any other container. The bags are opened and the barrels 12 are transferred to a barrel pre-sort stage 50 which typically includes dumping the barrels 12 into a sorting and orienting apparatus (not illustrated) such as a feeding bowl or the like.

After the barrels 12 are sorted and oriented as desired, they are conveyed to the next stage 52 which preferably is an air wash including de-ionized air followed by a vacuum which removes loose particulate matter from the interior of the barrels 12. Additionally, the de-ionized air reduces static within the barrels 12 which assists in removing particulate matter that may be clinging to the barrels 12. Alternatively, the particulate matter within the barrels 12 can be removed by any other method including use of a high pressure air, washing with water or other liquid.

The interior surface 40 of the barrels 12 is then provided with a coating of silicone in step 54 which preferably is applied by atomization. If desired, following atomization of silicone the barrels 12 can be heat cured for up to 1.5 hours to assist in providing a more even coating of silicon on the interior surface 40 of the barrels 12 which may or may not be necessary.

The stoppers 16 are washed, siliconized, steam sterilized and placed in bags or covered or sealed metal pans in step 56. The stoppers 16 then are transported into a Class 100,000 low particulate air room 58, illustrated in dotted lines in FIG. 2, where previous steps 52 and 54 of ionizing and siliconizing were performed.

The stoppers 16 then are inserted within a respective barrel 12 in step 60 until the stopper 16 "bottoms-out" or reaches the first end 20 of the barrel 12. The assembled barrels 12 and stoppers 16 then are transported to a filling line 62 which maintains a Class 100 standard during filling, preferably under a hood, curtain or the like.

The luer caps 14 are washed, siliconized, steam sterilized and placed in plastic bags or in covered or sealed metal pans in step 64 and are conveyed to the filling line 62 to be assembled to the barrels 12. It is to be noted that the components of the syringe 10 are not considered sterile at this point in the process.

As mentioned above, steam sterilizing of at least the stoppers 16, which preferably are made of rubber, is an important part of the present process. Such steam sterilization provides good microbial "kill" and also drives moisture into the rubber of the stoppers 16 which moisture subsequently is driven out of the stoppers 16 during terminal sterilization. It is particularly important that the moisture is driven out of the stopper 16 proximate the cylindrical side 34 having the ribs 38 to provide good microbial "kill" and a good seal therebetween.

Once a desired number of barrels 12, luer caps 14 and stoppers 16 are provided to the filling line 62, filling and sealing of the syringe 10 can begin. First, in step 66 the barrel 12 is filled with a desired medicament, imaging agent or other liquid through the port 26.

As the barrel 12 is being filled through the port 26 of the first end of the syringe, substantially no air inters the syringe barrel. At the same time, the stopper 16 is advanced toward the second end 22 of the barrel 12 by the pressure of the liquid until the exterior end 32 of the stopper 16 reaches a position bet approximately ⅛–½" from the second end 22 of the barrel 12. It is to be noted that, since the stopper 16 moves minimally within the barrel 12 during terminal sterilization, the stopper 16 can be extended to a position approximately flush with the second end 22 of the barrel 12 if desired.

Next, in step 68 the luer cap 14 is placed over the luer connector 28 to seal the port 26. In order to reduce the amount of air within the barrel 12, the medicament preferably completely fills the port 26 before the luer cap 14 is applied.

After filling the barrel 12, the barrel 12 can be labeled with lot numbers, dates or any other information in step 70. Preferably, such information is provided by laser or ink jet printing.

The syringe 10 then is conveyed to step 72 where it is inspected, particularly for medicament or solution between the ribs 38 of the stopper 16 and/or particulate matter within the medicament. If the syringe 10 passes inspection step 72, it is packed off into a stainless steel sterilization tray in step 74 where the trays could have some plastic components if desired.

A plurality of syringes 10 in the trays then are terminally sterilized in step 76, preferably in an autoclave (not illustrated). The particular type of autoclave utilized preferably includes a spray over-pressure cycle or a steam-air mixture cycle which maintains pressure about the exterior of the barrels 12 equal to or greater than the pressure in the interior of the barrels 12 during sterilization and preferably reaches a maximum temperature between 116° and 120° C.

The type of autoclave, pressure and maximum temperature range are determined beforehand and prevent the stopper 16 from moving out of the second end 22 of the barrel 12 while providing the desired sterilization of the syringe 10 and its contents. Additionally, the selected temperature range and autoclave do not provide significant movement of the stopper 16 toward the second open end 22 of the barrel 12 during terminal sterilization.

Following terminal sterilization, the syringes 10 are dried in step 78. Preferably, the syringes 10 are dried using a compressed, oil-free air (CAOF), but any type of drying can be employed, for example, utilization of a special drying cycle in an autoclave. If desired, an optional luer cover (not illustrated) can be applied in step 82.

At this point, plungers 18 can be provided in step 84 and attached to the recess 36 in the exterior end 32 of the stopper 16 in step 86. After the plunger 18 is attached, the syringes 10 are then inspected in step 88 for completeness and for any particulate within the medicament or solution in the barrel 12.

Labels are typically required for the syringes 10 and are preferably provided in roll form made of a pressure sensitive, clear plastic film, for example, Mylar. The labels are provided with a lot number and a date, preferably by hot stamping or ink jet coding.

The labels then may be inspected for the date and lot number either visually or by an electronic vision system (not illustrated). In step 96, the labels are applied to the barrels 12 or any other part of the syringe 10 and inspected for positioning and presence of the label on the syringe.

Following labeling, the syringes 10 are packed into individual cartons, bags or pouches in step 98, which can be labelled for lot number, expiration date and the like.

Accordingly, the above described process provides a terminally sterilized syringe 10 preferably in a straight line process, with minimization and preferably essentially elimination of air within the syringe 10. The terminal sterilization substantially reduces, if not eliminates, disadvantageous movement of the stopper 16 during autoclaving due to the over-pressure cycle and lower temperatures in the autoclave.

This also enables a more precise control of heat input and the use of materials for the barrel 12 and other members having higher clarity and improved impact strength which normally would distort at temperatures above 120° C. For example, if polypropylene is used to form the barrel 12, an improved clarity random polypropylene could not be used at higher temperatures because of distortion.

Figure 3:
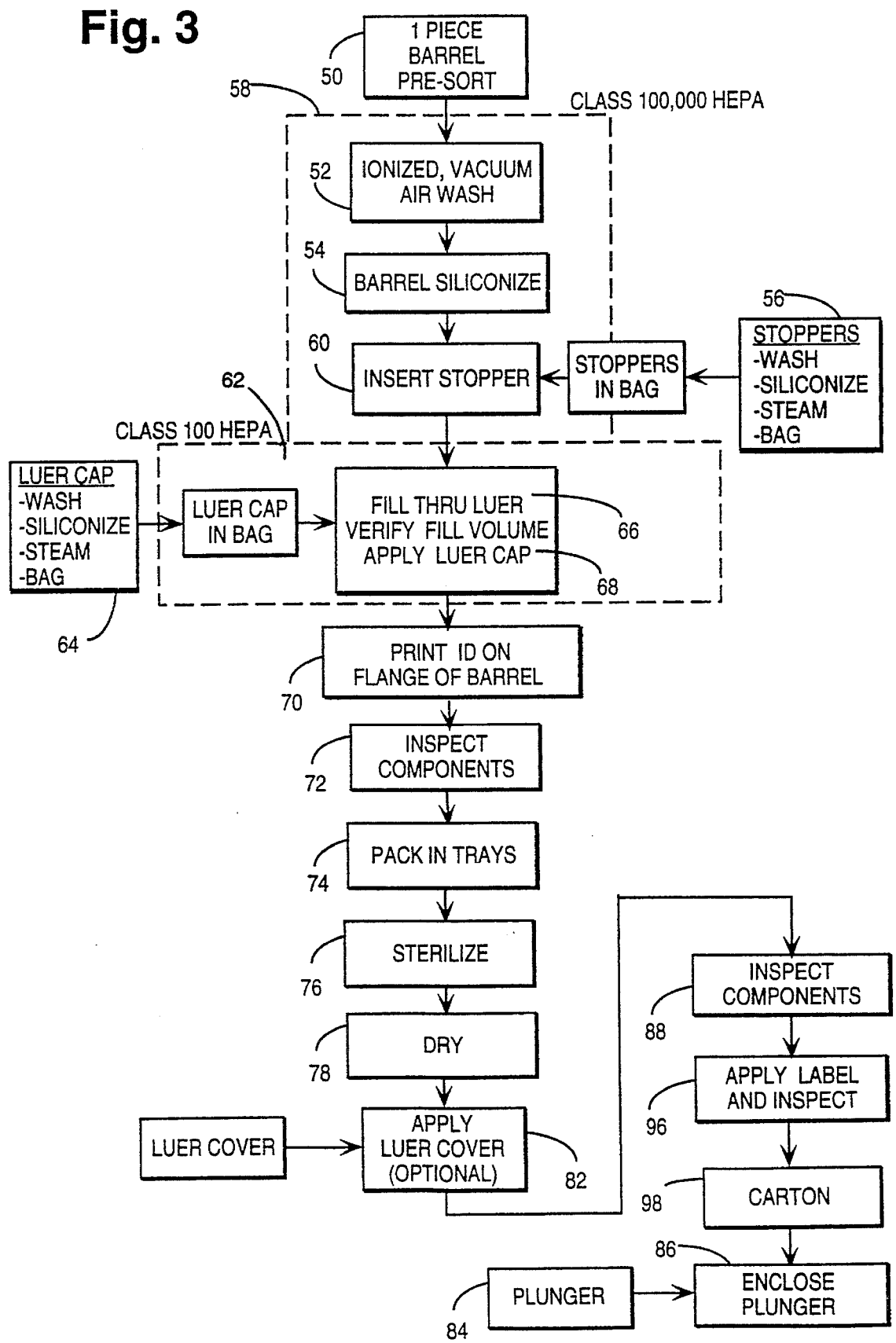
FIG. 3 is a flow chart illustrating another embodiment of the terminal sterilization process of the present invention.

FIG. 3 illustrates another embodiment of assembling, prefilling and terminally sterilizing according to the present invention. In this embodiment, plungers 18 preferably are enclosed in the carton. All other steps in this embodiment are substantially the same as in the embodiment of FIGS. 2a and 2b.

It will be readily apparent from the foregoing detailed description of the invention and from the illustrations thereof that numerous variations and modifications may be effected without departing from the true spirit and scope of the novel concepts or principles of this invention.

What is claimed is:

1. A method of prefilling and terminally sterilizing a syringe, consisting of the sequential steps of:
   a) providing an empty syringe barrel having first and second opposite ends, said first end having a port therethrough with a connector member formed about an exterior of said port and said second end being open;
   b) removing particulate matter from the interior of said syringe barrel;
   c) sterilizing a cap and a stopper, said stopper having first and second opposite longitudinal ends;
   d) prior to filling said empty syringe barrel, inserting said first end of said stopper into the second open end of said empty syringe barrel and moving said stopper toward said first end of said empty syringe barrel until said first end of said stopper reaches a position against said first end of said empty syringe barrel;
   e) prior to connecting the cap to the connector member to seal the port, filling said syringe barrel with a desired fluid medicament through said port of said first end of said syringe barrel wherein substantially no air enters said syringe barrel, said stopper moving from said first end to said second end of said syringe barrel by fluid pressure of said fluid medicament as the syringe barrel is filled;
   f) after filling the syringe barrel through the port, connecting said cap to said connector member of said first end of said filled syringe barrel to seal said port; and
   g) terminally sterilizing said prefilled and assembled syringe barrel, stopper and cap in an autoclave having a spray over-pressure cycle which maintains pressure about the exterior of said syringe barrel at least equal to the pressure within the interior of said syringe barrel.

2. The method in accordance with claim 1 wherein step e) includes filling said syringe barrel so that said second end of said stopper is substantially flush with said second end of said syringe barrel.

3. The method in accordance with claim 1 wherein step b) includes removing particulate matter with a de-ionized air wash.

4. The method in accordance with claim 1 wherein said terminal sterilization of step g) includes placing said syringe barrel, stopper and cap into an autoclave having a maximum temperature of between 116° and 120° C. for a predetermined period of time.

5. The method in accordance with claim 1 wherein said syringe barrel is formed from plastic.

6. The method in accordance with claim 1 including prior to step d) coating said interior of said syringe barrel with silicone by atomization.

7. The method in accordance with claim 1 wherein step c) includes washing, siliconizing and steam sterilizing said cap and said stopper.

8. The method in accordance with claim 1 that further comprises step h) drying said syringe barrel, said stopper and said cap using compressed, oil-free air.

9. The method in accordance with claim 8 that further comprises step i) attaching a plunger to said second end of said stopper.

10. The method in accordance with claim 9 that further comprises step j) applying a label to an outside surface of said syringe barrel.

\* \* \* \* \*